United States Patent
Bao et al.

(10) Patent No.: US 10,295,498 B2
(45) Date of Patent: May 21, 2019

(54) AIR DRYER FOR ION MOBILITY SPECTROMETER

(71) Applicant: Nuctech Company Limited, Haidian District, Beijing (CN)

(72) Inventors: Yuntai Bao, Beijing (CN); Yangtian Zhang, Beijing (CN); Jianhu Ma, Beijing (CN); Haichao Zhou, Beijing (CN); Wangyang Wu, Beijing (CN); Wen He, Beijing (CN); Zhongxia Zhang, Beijing (CN); Bin Xue, Beijing (CN)

(73) Assignee: NUCTECH COMPANY LIMITED, Haidian District, Beijing (CN)

( * ) Notice: Subject to any disclaimer, the term of this patent is extended or adjusted under 35 U.S.C. 154(b) by 239 days.

(21) Appl. No.: 15/116,753

(22) PCT Filed: Jun. 18, 2015

(86) PCT No.: PCT/CN2015/081772
§ 371 (c)(1),
(2) Date: Aug. 4, 2016

(87) PCT Pub. No.: WO2016/034007
PCT Pub. Date: Mar. 10, 2016

(65) Prior Publication Data
US 2016/0349211 A1 Dec. 1, 2016

(30) Foreign Application Priority Data
Sep. 4, 2014 (CN) .......................... 2014 1 0448970

(51) Int. Cl.
*B01D 53/02* (2006.01)
*G01N 27/62* (2006.01)
(Continued)

(52) U.S. Cl.
CPC ....... *G01N 27/622* (2013.01); *B01D 53/0438* (2013.01); *B01D 53/261* (2013.01); *B01D 2257/80* (2013.01); *B01D 2259/4009* (2013.01)

(58) Field of Classification Search
CPC ........ B01D 2257/80; B01D 2259/4009; B01D 53/0438; B01D 53/261; G01N 27/622
See application file for complete search history.

(56) References Cited

U.S. PATENT DOCUMENTS 3,850,592 A * 11/1974 Huffman .............. B01D 53/261
95/123
5,405,781 A * 4/1995 Davies ................. G01N 27/622
250/282
(Continued)

FOREIGN PATENT DOCUMENTS

CN 101992008 A 3/2011
CN 102074448 A 5/2011
(Continued)

OTHER PUBLICATIONS

International Search Report for corresponding International Patent Application No. PCT/CN2015/081772 dated Sep. 24, 2015, 6pgs.
(Continued)

*Primary Examiner* — Christopher P Jones
(74) *Attorney, Agent, or Firm* — Merchant & Gould P.C.

(57) ABSTRACT

Embodiments of the present invention provide an air dryer for an ion mobility spectrometer, comprising a heating element used to heat a thermal conduction device, thereby heating the desiccant. Embodiments of the present invention further provide a regeneration method, by which the operation mode of the ion mobility spectrometer may be switched, so that during a non-working time of the ion mobility spectrometer, the desiccant is heated and thereby regenerated. With the present invention, the desiccant is avoided from being regularly replaced, thereby improving the per-
(Continued)

formance and increasing the service life of the dryer. Regeneration of the desiccant is performed by making full use of the non-working time of the ion mobility spectrometer without affecting normal operation of instrument.

14 Claims, 2 Drawing Sheets

(51) Int. Cl.
*B01D 53/26* (2006.01)
*B01D 53/04* (2006.01)

(56) References Cited

U.S. PATENT DOCUMENTS

| | | | | |
|---|---|---|---|---|
| 6,642,513 | B1* | 11/2003 | Jenkins | B01D 53/30 250/281 |
| 2008/0191132 | A1* | 8/2008 | Boyle | G01N 27/624 250/287 |
| 2011/0036973 | A1* | 2/2011 | Alonso | G01N 27/624 250/282 |
| 2011/0289944 | A1 | 12/2011 | Ouyang et al. | |
| 2013/0234013 | A1* | 9/2013 | Patterson | G01N 1/2205 250/282 |
| 2015/0362228 | A1* | 12/2015 | Ivashin | F25B 21/02 62/601 |

FOREIGN PATENT DOCUMENTS

| | | |
|---|---|---|
| CN | 102313776 A | 1/2012 |
| CN | 103308590 A | 9/2013 |
| CN | 104201083 A | 12/2014 |
| CN | 204118032 U | 1/2015 |
| WO | 2006/110700 A1 | 10/2006 |

OTHER PUBLICATIONS

Extended European Search Report for corresponding European Patent Application No. 15834705.4 dated Jun. 29, 2017, 7 pages.
Second Australian Office Action for corresponding Australian Patent Application No. 2015306581 dated Feb. 23, 2017, 3 pgs.
Australian Office Action for corresponding Australian Patent Application No. 2015306581 dated Aug. 19, 2016, 2 pgs.
Chinese Office Action for corresponding Chinese Patent Application No. 201410448970.8 dated Mar. 22, 2016, 9 pgs.

* cited by examiner

AIR DRYER FOR ION MOBILITY SPECTROMETER

This application is a National Stage Application of PCT/CN2015/081772, filed 18 Jun. 2015, which claims benefit of Serial No. 201410448970.8, filed 4 Sep. 2015 in China and which applications are incorporated herein by reference. A claim of priority is made to each of the above disclosed applications.

BACKGROUND OF THE INVENTION

Technical Field

The present disclosure generally relates to the field of sample analysis, and particularly, to an air drying apparatus in an ion mobility spectrometer.

Description of the Related Art

During analyzing a sample by using an ion mobility spectrometer, air is inputted as a carrier gas into an ion migration tube of the ion mobility spectrometer, and the air is dried before inputted into an ion migration tube. The air is first inputted to an air dryer, and the air dried by the air dryer is inputted into the ion migration tube. For the dryer, a desiccant needs to be replaced after many operations, which will adversely affect performances of the dryer.

SUMMARY OF THE INVENTION

In order to solve the above and other problems in prior arts, embodiments of the present disclosure provide an air dryer for an ion mobility spectrometer and an ion mobility spectrometer, which remove the need of regularly replacing the desiccant, thereby improving performances of the dryer. Regeneration process of the desiccant is performed by making full use of a non-working time of the ion mobility spectrometer, without affecting normal operation of instruments.

In order to achieve the above object, embodiments of the present disclosure provide the following technique solutions: an air dryer for an ion mobility spectrometer comprises: a housing; a gas inlet provided in the housing, through which air enters the air dryer; a gas outlet provided in the housing, the gas outlet communicating with an ion migration tube of the ion mobility spectrometer so that dried air enters the ion migration tube through the gas outlet; a desiccant chamber disposed within the housing, a desiccant being arranged within the desiccant chamber to dry the air entering through the gas inlet; a thermal conduction device disposed within the desiccant chamber and surrounded by the desiccant; and a heating element disposed within the thermal conduction device and configured to heat thermal conduction device.

In one embodiment of the present disclosure, the air dryer further comprises: a water cooling device configured to cool the air dryer; a water cooling connection port provided in the housing, through which cooling water from the water cooling device flows into the air dryer and through which the cooling water flows out of the air dryer to return to the water cooling device; and a cooling water passage arranged within the housing, the cooling water flowing through the cooling water passage.

In one embodiment of the present disclosure, the housing comprises an end cover, which is connected with a body of the housing in a sealed way and on which the gas inlet, the gas outlet and the water cooling connection port are provided.

In one embodiment of the present disclosure, air dryer further comprises a thermal insulating layer disposed between the housing and the desiccant chamber.

In one embodiment of the present disclosure, helical fins are provided on a surface of the thermal conduction device.

In one embodiment of the present disclosure, the desiccant is a molecular sieve.

In one embodiment of the present disclosure, the housing is cylindrical and the desiccant chamber is cylindrical.

In one embodiment of the present disclosure, there is provided an ion mobility spectrometer comprising the air dryer as described above.

In one embodiment of the present disclosure, there is provided method of regenerating a gas desiccant in an air dryer, the air dryer being the air dryer as described above and used for the ion mobility spectrometer, the method comprising steps of: heating up the heating element to heat the desiccant during a non-working time of the ion mobility spectrometer; inputting air into the dryer while heating the desiccant; and stopping heating after heating the desiccant for a predefined time.

In one embodiment of the present disclosure, the method of regenerating a gas desiccant in an air dryer air dryer further comprises a step of: cooling the air dryer by a cooling device after stopping heating.

In one embodiment of the present disclosure, the heating element is heated up to a temperature in a range of 150° C.~400° C.

In one embodiment of the present disclosure, the heating element is heated up within 30 minutes and is kept at 400° C.

In one embodiment of the present disclosure, the predefined time used to heat is in a range of 30 minutes to 2 hours.

In one embodiment of the present disclosure, in the step of cooling the air dryer by the cooling device, the cooling device is configured to reduce a temperature of the air dryer to an operating allowable temperature within 2 hours.

BRIEF DESCRIPTION OF THE DRAWINGS

The above and other objects and advantages of the present disclosure will become more apparent and more clearly understood by describing in detail exemplary embodiments thereof with reference to the accompanying drawings. In the following description, the same reference numerals in the drawings denote the same components.

DETAILED DESCRIPTION OF PREFERRED EMBODIMENTS OF THE INVENTION

The present disclosure will be described further hereinafter in detail with reference to the embodiments in combination with attached drawings. The following embodiments are intended to illustrate the present disclosure, and are not intended to limit scopes of the present disclosure.

Embodiments of the present disclosure provide an air dryer for an ion mobility spectrometer, comprising: a housing; a gas inlet provided in the housing, through which air enters the air dryer; a gas outlet provided in the housing, the gas outlet communicating with an ion migration tube of the ion mobility spectrometer so that dried air enters the ion migration tube through the gas outlet; a desiccant chamber disposed within the housing, a desiccant being arranged within the desiccant chamber to dry the air entering through the gas inlet; a thermal conduction device disposed within the desiccant chamber and surrounded by the desiccant; and a heating element disposed within the thermal conduction device and configured to heat thermal conduction device.

Figure 1:
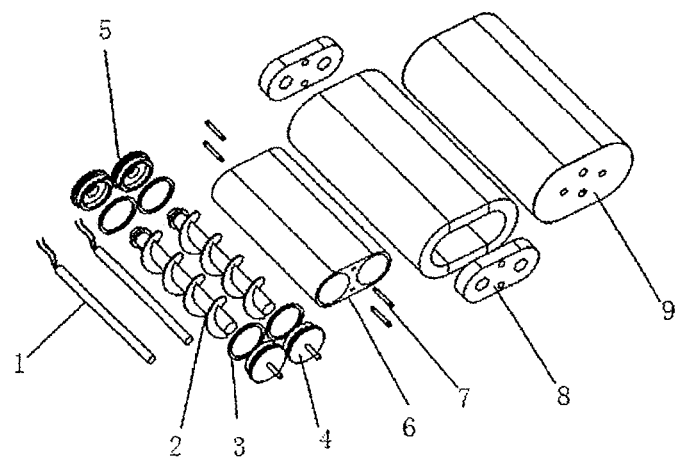
FIG. 1 is an exploded view of an air dryer provided according to an embodiment of the present disclosure.

FIG. 1 is an exploded view of an air dryer provided according to an embodiment of the present disclosure. Here, it is noted by the applicant that structures shown in FIG. 1 are not intended to limit the present disclosure; in other words, the structures shown in FIG. 1 are not necessarily required in the present disclosure, and changes and substitutions may be made by those skilled in the art to the structures shown in FIG. 1 based on concepts of the present disclosure.

Figure 2:
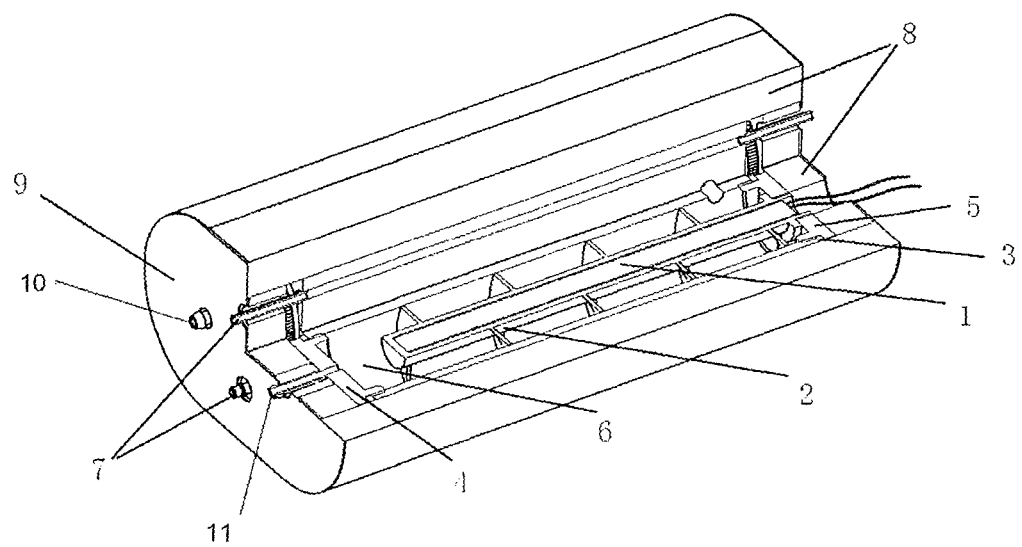
FIG. 2 is an assembled schematic diagram of an air dryer provided according to an embodiment of the present disclosure, with some structures removed for illustration.

FIG. 2 is an assembled diagram of the structures shown in FIG. 1, with parts removed for illustration. As shown in FIG. 1 and FIG. 2, an air dryer for an ion mobility spectrometer, comprising: a housing 9; a gas inlet 10 provided in the housing 9, through which air enters the air dryer; a gas outlet 11 provided in the housing 9, the gas outlet 11 communicating with an ion migration tube (not shown in the figures) of the ion mobility spectrometer so that dried air enters the ion migration tube through the gas outlet 11; a desiccant chamber 6 disposed within the housing 9, a desiccant being arranged within the desiccant chamber 6 to dry the air entering through the gas inlet 10; a thermal conduction device 2 disposed within the desiccant chamber 6 and surrounded by the desiccant; and a heating element 1 disposed within the thermal conduction device 2 and configured to heat thermal conduction device.

As shown in FIG. 1, the heating element 1 may be a heating bar, which is arranged within the thermal conduction device and is isolated from the dryer. The heating bar is quickly heated up, so that heat is transferred to the desiccant through the thermal conduction device, thereby heating the desiccant. During this, air passes through an air heater and carries moisture away from the desiccant due to the heating effect of the heating bar, so that the desiccant is regenerated.

In one embodiment of the present disclosure, as shown in FIGS. 1 and 2, the air dryer further comprises: a water cooling device (not shown) configured to cool the air dryer; a water cooling connection port 7 provided in the housing 9, through which cooling water from the water cooling device flows into the air dryer and through which the cooling water flows out of the air dryer to return to the water cooling device; and a cooling water passage (not shown) arranged within the housing, through which the cooling water flows. Position and shape of the cooling water passage may be set by those skilled in the art as desired to meet cooling requirement.

Here, the water cooling device may be a water cooling device in prior arts and may be commercially available. After the dryer is stopped from being heated by the heating element, the dryer may be cooled by using the water cooling device, thereby the dryer cools down so that it can be reused in cooperation with the ion mobility spectrometer.

In one embodiment of the present disclosure, as shown in FIGS. 1 and 2, the housing 9 comprises end covers 4 and 5 (a front end cover 4 and a rear end cover 5), which are connected with a body of the housing in a sealed way and on which the gas inlet, the gas outlet and the water cooling connection port are provided.

A sealing gasket 3 may be arranged to provide a better sealing between the end covers and the body of the housing.

In one embodiment of the present disclosure, as shown in FIGS. 1 and 2, the air dryer further comprises a thermal insulating layer 8 disposed between the housing 9 and the desiccant chamber 6. The thermal insulating layer 8 is used to enable heat insulation and preservation of the air dryer.

In one embodiment of the present disclosure, as shown in FIGS. 1 and 2, helical fins are provided on a surface of the thermal conduction device 2. The thermal conduction device and the helical fins are made of metal materials such as copper, for providing quick heat dissipation; in addition, the helical fins can provide uniform heat dissipation and facilitate to guide gas flow so that the gas flow sufficiently contacts with the desiccant.

In one embodiment of the present disclosure, the desiccant is a molecular sieve filled up the desiccant chamber.

In one embodiment of the present disclosure, as shown in FIGS. 1 and 2, the housing is cylindrical and the desiccant chamber is cylindrical.

In one embodiment of the present disclosure, there is provided an ion mobility spectrometer comprising the air dryer as described above.

In one embodiment of the present disclosure, there is provided a method of regenerating a gas desiccant in an air dryer, the air dryer being the air dryer as described above and used for the ion mobility spectrometer, the method comprising steps of: heating up the heating element to heat the desiccant during a non-working time of the ion mobility spectrometer; inputting air into the dryer while heating the desiccant; and stopping heating after heating the desiccant for a predefined time.

In one embodiment of the present disclosure, the method of regenerating a gas desiccant in an air dryer further comprises a step of: cooling the air dryer by a cooling device after stopping heating.

In one embodiment of the present disclosure, the heating element is heated up to a temperature in a range of 150° C.~400° C.

In one embodiment of the present disclosure, the heating element is heated up within 30 minutes and is kept at 400° C.

In one embodiment of the present disclosure, the predefined time used to heat is in a range of 30 minutes to 2 hours.

In one embodiment of the present disclosure, in the step of cooling the air dryer by the cooling device, the cooling device is configured to reduce a temperature of the air dryer to an operating allowable temperature within 2 hours.

Operations of ion mobility spectrometer and the air dryer according to the present disclosure will be briefly described.

Figure 3:
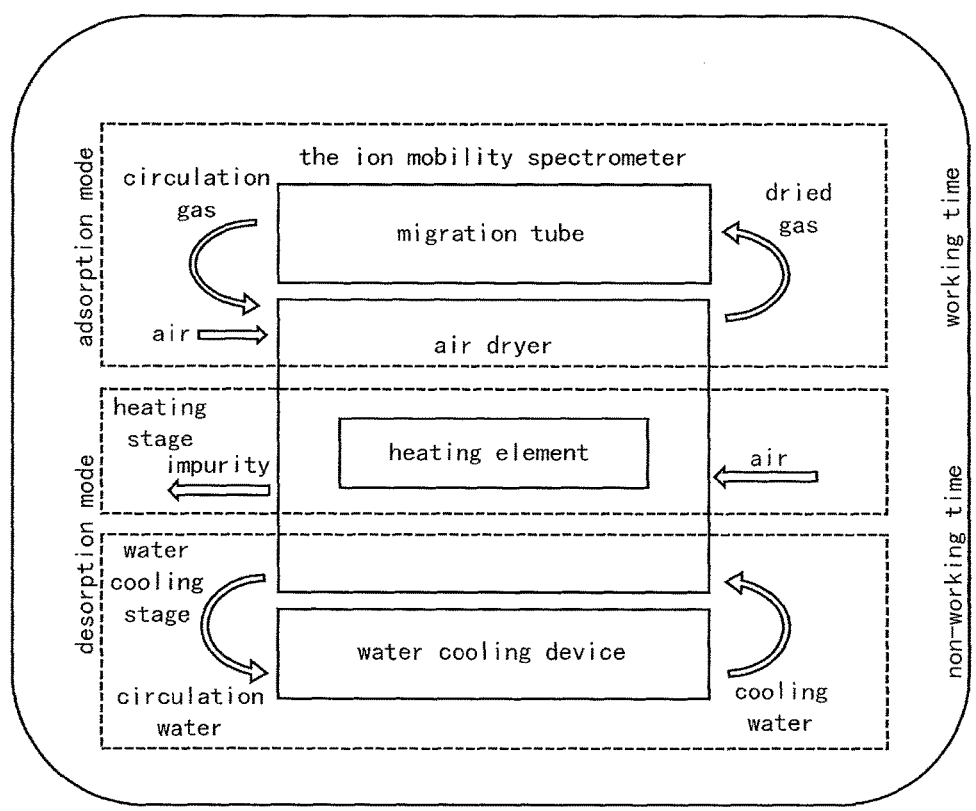
FIG. 3 is a schematic diagram illustrating a working principle of an ion mobility spectrometer comprising an air dryer provided according to an embodiment of the present disclosure.

As shown in FIG. 3, the ion mobility spectrometer comprises a migration tube and a dryer. When the ion mobility spectrometer is in a working state, that is, during a working time of the ion mobility spectrometer, the air dryer is in an adsorption mode, in which circulation gas and air enter the air dryer, dried gas discharged from the air dryer enters the migration tube, the heating element in the air dryer is not operated, the air passes through the air dryer so as to be dried by the desiccant, and dried air is used as a carrier gas for the ion mobility spectrometer.

During a non-working time of the ion mobility spectrometer, the air dryer is in a desorption mode, in which the heating element in the air dryer provides heating operation, while air is introduced into the dryer, so that the desiccant in the dryer is heated and moisture is carried away from the desiccant by the air, thereby the desiccant is regenerated. According to an embodiment of the present disclosure, a water cooling device is further included. Heating operation is stopped after heating for a certain time, and the water cooling device is turned on to enter a water cooling stage, so that the air dryer is quickly cooled down, thereby the air dryer can be reused in cooperation with the ion mobility spectrometer.

With the air dryer provided according the embodiments of the present disclosure, the desiccant is avoided from be regularly replaced and can be regenerated, thereby avoiding disassembly of the dryer and increasing service life of the dryer; regeneration of the desiccant may be performed during the non-working time of the ion mobility spectrometer, without occupying the working time of the ion mobility spectrometer.

The above described contents are only exemplary embodiments of the present disclosure, but scopes of the present disclosure will not limited to those. It would be appreciated by those skilled in the art that various changes or modifications, which may be easily made without departing from the principles and spirit of the disclosure, fall within the scope of the present disclosure. Thus, the scopes of the present invention are defined in the claims and their equivalents.

What is claimed is:

1. An air dryer for an ion mobility spectrometer, comprising:
   a housing;
   a gas inlet provided in the housing, through which air enters the air dryer;
   a gas outlet provided in the housing, the gas outlet communicating with an ion migration tube of the ion mobility spectrometer so that dried air enters the ion migration tube through the gas outlet;
   a desiccant chamber disposed within the housing, a desiccant being arranged within the desiccant chamber to dry the air entering through the gas inlet;
   a thermal conduction device disposed within the desiccant chamber and surrounded by the desiccant; and
   a heating element disposed within an interior portion of the thermal conduction device and configured to heat thermal conduction device,
   wherein the interior portion of the thermal conduction device is isolated from the air.

2. The air dryer according to claim 1, further comprising:
   a water cooling device configured to cool the air dryer;
   a water cooling connection port provided in the housing, through which cooling water from the water cooling device flows into the air dryer and through which the cooling water flows out of the air dryer to return to the water cooling device; and
   a cooling water passage arranged within the housing, the cooling water flowing through the cooling water passage.

3. The air dryer according to claim 2, wherein
   the housing comprises an end cover, which is connected with a body of the housing in a sealed way and on which the gas inlet, the gas outlet and the water cooling connection port are provided.

4. The air dryer according to claim 1, further comprising:
   a thermal insulating layer disposed between the housing and the desiccant chamber.

5. The air dryer according to claim 1, wherein helical fins are provided on a surface of the thermal conduction device.

6. The air dryer according to claim 1, wherein the desiccant is a molecular sieve.

7. The air dryer according to claim 1, wherein the housing is cylindrical and the desiccant chamber is cylindrical.

8. An ion mobility spectrometer, comprising the air dryer of claim 1.

9. A method of regenerating a gas desiccant in an air dryer, the air dryer being the air dryer of claim 1 and used for the ion mobility spectrometer, the method comprising steps of:
   heating up the heating element to heat the desiccant during a non-working time of the ion mobility spectrometer;
   inputting air into the dryer while heating the desiccant; and
   stopping heating after heating the desiccant for a predefined time.

10. The method according to claim 9, further comprising a step of:
    cooling the air dryer by a cooling device after stopping heating.

11. The method according to claim 9, wherein
    the heating element is heated up to a temperature in a range of 150° C.~400° C.

12. The method according to claim 11, wherein the heating element is heated up within 30 minutes and is kept at 400° C.

13. The method according to claim 9, wherein the predefined time used to heat is in a range of 30 minutes to 2 hours.

14. The method according to claim 10, wherein in the step of cooling the air dryer by the cooling device, the cooling device is configured to reduce a temperature of the air dryer to an operating allowable temperature within 2 hours.

* * * * *